US008630425B2

(12) United States Patent
Chang et al.

(10) Patent No.: US 8,630,425 B2
(45) Date of Patent: Jan. 14, 2014

(54) APPARATUS, SYSTEM, AND METHOD FOR AUDIO COMMUNICATIONS

(75) Inventors: Sheng-Chiao Chang, Irvine, CA (US); Frank Hung, Tustin, CA (US); Dan T. Wang, Irvine, CA (US)

(73) Assignee: Cisco Technology, Inc., San Jose, CA (US)

( * ) Notice: Subject to any disclaimer, the term of this patent is extended or adjusted under 35 U.S.C. 154(b) by 860 days.

(21) Appl. No.: 12/333,753

(22) Filed: Dec. 12, 2008

(65) Prior Publication Data

US 2010/0150368 A1 Jun. 17, 2010

(51) Int. Cl.
*A61F 11/06* (2006.01)

(52) U.S. Cl.
USPC .......................................... 381/71.6; 381/71.1

(58) Field of Classification Search
USPC ........ 381/71.1, 71.6, 71.8; 181/128, 130, 135
See application file for complete search history.

(56) References Cited

U.S. PATENT DOCUMENTS

2003/0069048 A1* 4/2003 Liu et al. ........................ 455/569
2004/0121796 A1* 6/2004 Peng ............................. 455/522
2005/0220319 A1 10/2005 Chan et al.
2006/0029234 A1* 2/2006 Sargaison ........................ 381/74
2006/0045304 A1* 3/2006 Lee et al. ....................... 381/384
2006/0233413 A1* 10/2006 Nam ............................. 381/380
2007/0036367 A1* 2/2007 Ko ............................... 381/71.1
2007/0036376 A1 2/2007 Fried
2007/0207796 A1 9/2007 Yan
2007/0281744 A1* 12/2007 Andreasson .................. 455/557
2007/0297618 A1* 12/2007 Nurmi et al. ................. 381/71.6
2008/0002835 A1 1/2008 Sapiejewski et al.
2008/0080705 A1* 4/2008 Gerhardt et al. .............. 379/430
2008/0158000 A1* 7/2008 Mattrazzo ................ 340/825.25
2008/0170738 A1 7/2008 Hope et al.
2009/0124286 A1* 5/2009 Hellfalk et al. ............ 455/556.1
2009/0176540 A1* 7/2009 Do et al. .................... 455/575.2
2010/0020982 A1* 1/2010 Brown et al. .................... 381/74
2010/0046767 A1* 2/2010 Bayley et al. ................... 381/59
2010/0128887 A1* 5/2010 Lee et al. ........................ 381/74

OTHER PUBLICATIONS

Chad Shmukler, "My iPhone sometimes stops outputting sound after I remove my earbuds/headphones? How can I fix this?" Pub. Feb. 24, 2008, http://www.iphonefaq.org/archives/97379, 1 page.

* cited by examiner

*Primary Examiner* — Joseph Chang
*Assistant Examiner* — Jeffrey Shin
(74) *Attorney, Agent, or Firm* — Patent Capital Group

(57) ABSTRACT

An apparatus is provided in one example embodiment and includes an earpiece that includes at least one switch that senses physical contact with an end user operating the apparatus. The contact triggers an application to be initiated for the apparatus. In more specific embodiments, one or more additional switches are provided to sense physical contact from the end user and trigger the application based on at least two of the switches sensing the contact. In still other embodiments, a microphone is provided and is coupled to a body element and operable to receive voice data from the end user.

22 Claims, 4 Drawing Sheets

APPARATUS, SYSTEM, AND METHOD FOR AUDIO COMMUNICATIONS

TECHNICAL FIELD OF THE INVENTION

This invention relates in general to the field of communications and, more particularly, to an apparatus, a system, and a method for audio communications.

BACKGROUND OF THE INVENTION

In response to safety concerns and recently passed legislation, hands free devices have emerged into the marketplace. A hands free device is typically used with cell phones, which permit the user to talk on the phone without holding it. Through the assistance of the hands free device, the user can let the phone lie in one area while talking into a microphone attached to some type of earpiece. In order to listen to the person on the other end, the user normally has an earbud speaker placed in one ear.

A hands free device has many benefits. For the multi-tasker, the hands free device makes it possible to easily move about and complete other tasks while talking on a corresponding device. The hands free device also makes it easier for the user to take notes or to type on the computer while talking on the phone.

Any hands free device should be responsive and easy to manage. Poor designs can cause an end user to fumble around when trying to initiate an application (e.g., to answer an incoming phone call). These will only increase distractions for the end user and, in some cases, inhibit an end user from initiating an application.

BRIEF DESCRIPTION OF THE DRAWINGS

To provide a more complete understanding of the present invention and features and advantages thereof, reference is made to the following description, taken in conjunction with the accompanying figures, wherein like reference numerals represent like parts, in which.

DETAILED DESCRIPTION OF EXAMPLE EMBODIMENTS

Overview

An apparatus is provided in one example embodiment and includes an earpiece that includes at least one switch that senses physical contact with an end user operating the apparatus. The contact triggers an application to be initiated (i.e., triggered) for the apparatus. In more specific embodiments, one or more additional switches are provided to sense physical contact from the end user and then trigger the application based on at least two of the switches sensing the contact. In still other embodiments, a microphone is provided and is coupled to a body element and operable to receive voice data from the end user.

Figure 1:
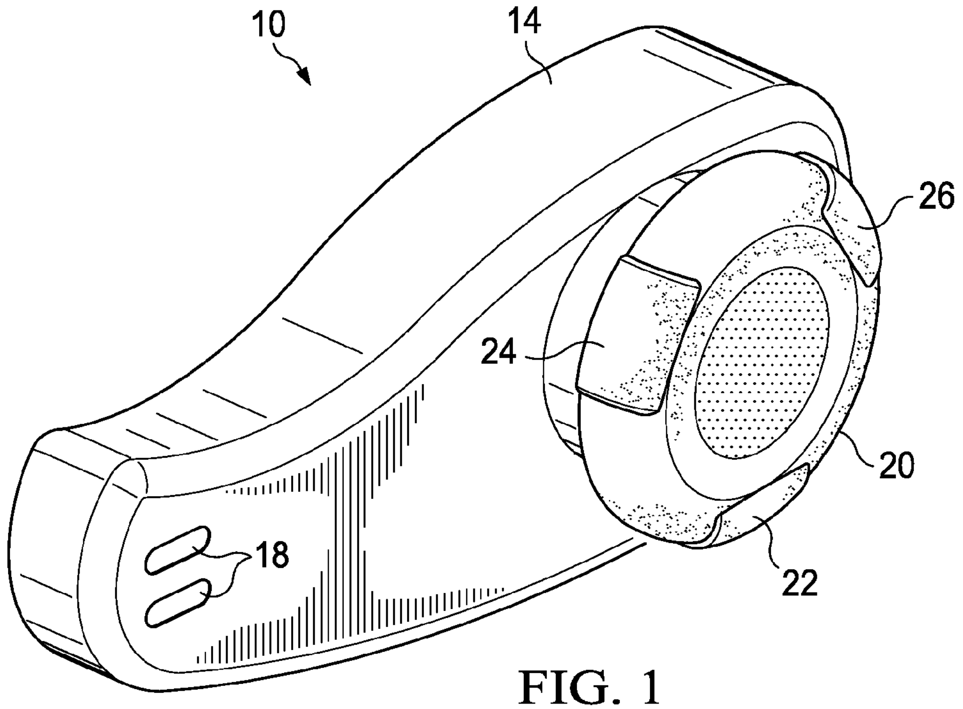
FIG. 1 is a simplified block diagram of an apparatus for audio communication in accordance with one embodiment of the present invention.

Turning to FIG. 1, FIG. 1 is a simplified block diagram of an apparatus 10 for audio communications. Apparatus 10 includes a body element 14, which is coupled to a microphone 18 and an earpiece 20. Earpiece 20 includes a set of switches 22, 24, and 26. Body element 14 can be made of any type of plastic, alloy, composite or other material that offers a housing or protection of some type for apparatus 10. Microphone 18 can include circuitry, hardware, software, codecs, etc. to facilitate the functions thereof in processing and/or coordinating voice data. Earpiece 20 can be any type of auditory element (e.g., an earbud, headphones, a single earphone, etc.) that allows the end user to hear audio information.

For purposes of illustrating the techniques of apparatus 10, it is important to understand the communications that may be in an audio environment. The following foundational information may be viewed as a basis from which the present invention may be properly explained. Such information is offered earnestly for purposes of explanation only and, accordingly, should not be construed in any way to limit the broad scope of the present invention and its potential applications.

Typically, there are different operation modes for a headset when it is placed on the ear and when it is taken off the ear. The operation of the device for which these headsets are connected often needs to be modified when the location of the headset changes. For example, when a headset used for mobile phones is placed in the ear, the operator of the phone may need to depress an Answer button on the phone to initiate a conversation. In other instances, when a headset is used for portable music playback devices, when it is taken off the ear, the operator of the device may need to press a Stop button, a Power Off button, or a Pause button.

As can readily be appreciated, there is some interim of time that the end user should seize when he attempts to engage/disengage the device. Were he not to properly account for this, then the device could remain in an ON position while the device is not being used. Reciprocally, if this time interval is not coordinated in a responsive manner, applications are not timely triggered (e.g., in a cellular telephone scenario, calls could be missed as the end user is attempting to find and press the button to initiate an application). Many protocols require an end user to press and actually hold a button (e.g., several seconds) before an application is even triggered.

In accordance with the techniques and teachings of the present invention, apparatus 10 provides a communication approach that can automatically trigger an action (e.g., a preprogrammed action) when it detects the change of location of apparatus 10 (on the ear, or off the ear). This triggering could be used for a music application, to connect an incoming call, for a speech recognition application, a dictation application, or any other suitable auditory application where apparatus 10 would be applicable. Note that, as used herein in this Specification, the term 'trigger' and 'initiate' are interchangeable.

Apparatus 10 can be aware of its location, as it can detect whether it is on the operator's ear or if it is off the ear. The detection mechanism can include one or more switches (e.g., #22, #24, and #26) that can detect in ear or out of ear operation, and trigger a predetermined action (e.g., trigger an application) based on its status.

One example of a suitable switch is a capacitance switch that detects changes in capacitance when contact with the skin is made. Apparatus 10 could leverage any such contact technology (e.g., technologies associated with a laptop touch pad) in order to achieve this contact protocol. In one example case, there could be several switches on apparatus 10, where all the switches are activated to trigger some action (e.g., turn ON an application). By configuring apparatus 10 in such a manner such that at least two of the switches need to be contacted in order for the application to trigger, accidental operation is avoided. In a similar endeavor, by removing contact (or pressure) from switches 22, 24, and/or 26, an application could be turned OFF or paused.

Switches 22, 24, and 26 can be located strategically to each other to avoid false detections during handling (e.g., inadvertent contact in an end user's pocket, briefcase, purse, etc.). False detections could cause unnecessary power drainage (e.g., depleting battery resources). As identified previously, switches 22, 24, and 26 could be capacitance switch that use some type of contact as a triggering event (for turning ON, OFF, or pausing an application). Other technologies that could be used in conjunction with apparatus 10 include pressure switches, frequency switches, temperature switches, voltage switches, or motion switches. All such substitutions are clearly within the broad scope of the present invention.

Figure 2A:
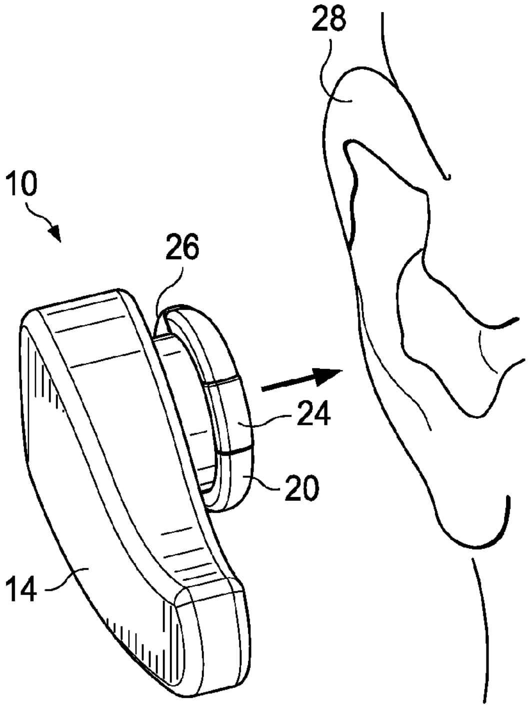
FIGS. 2A-2B are simplified block diagrams of an example implementation for the apparatus in accordance with one embodiment of the present invention.
Figure 2B:
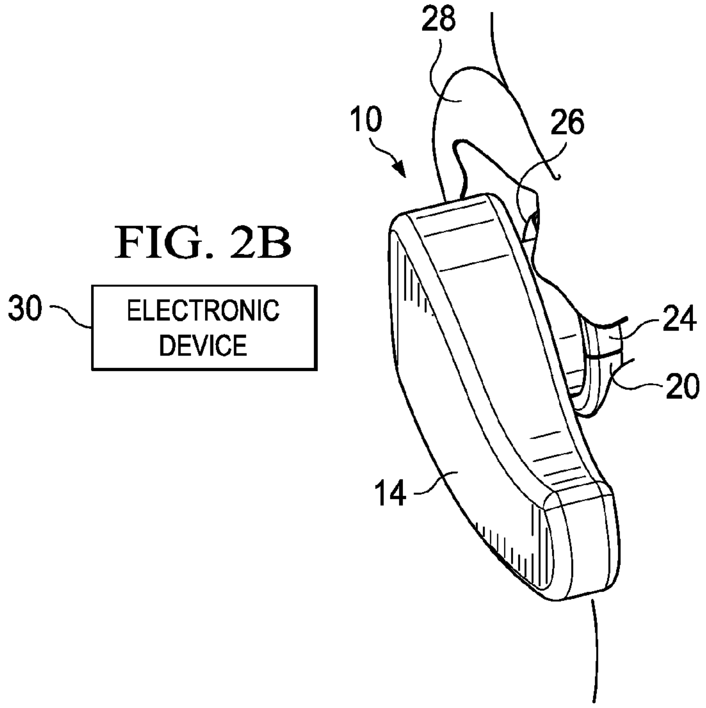

FIGS. 2A-2B are simplified block diagrams that are depicting an example implementation of apparatus 10. Note that such a solution does not detect the actual location of the headset, but triggers an action when it detects changes in how apparatus 10 is connected. Such a solution could be used with electronic device 30. Examples of electronic device 30 include portable music devices (I-Pod, I-Phone, I-Shuffle, Walkman music devices, Sony music devices, MP3 and MP4 players, etc.), wireless phones, desktop phones, domestic cordless phones, any electronic device that employs an earpiece, and any other item where responsiveness is an issue in triggering an application.

The placement of the switch to detect when earpiece 20 is being used is important. As apparatus 10 is inserted in the ear, one or more switches can either complete a small circuit, or be depressed such that an application is triggered to do some action (e.g., turn ON, turn OFF, pause, etc.). For the depressing type of switch, the one or more switches should be located in a position on the earpiece that would cause the switch to turn ON when the earpiece is worn. In one example implementation, the location of the switch(es) could be located on the perimeter of earpiece 20, or on the surface of earpiece 20 such that they would be depressed (or contacted) by the ear when earpiece 20 is engaged by an end user. This is illustrated in FIG. 2B.

In another embodiment, switches 22, 24, and 26 are touch switches that trigger an application based on contact (e.g., an end user's ear). In yet another embodiment, switches 22, 24, and 26 include (or be coupled to) a frequency component, where a change in background noise is detected when the ear is sealed off. Such a concept is somewhat similar to noise-cancelling earphones where the device would determine a constant background noise frequency, and send an inverse phase signal to cancel out the noise. In a similar fashion, microphone 18 and/or earpiece 20 can identify background noise, and when earpiece 20 is placed inside the ear, creating a seal, the background noise would decrease significantly, thus identifying that earpiece 20 is placed inside the ear. Accidental operation could also be avoided by setting a higher threshold for the attenuation of background noise in order for actions to be triggered.

In one non-limiting example embodiment, several equidistant capacitance switches are part of the switch design. Other designs use a simple pressure switch, where depressing a sensor connected to the switch activates an application. Note that any type of sensor (which helps to coordinate the operation of one or more of the switches discussed herein) may be included within the term 'switch' as used herein in this Specification. Similarly, corresponding circuitry (inclusive of appropriate hardware and software) is meant to be encompassed within the term 'switch' as used herein in this Specification.

Note also that the increase in the number of switches (e.g., from one to three) should further ensure that apparatus 10 does not create a false detection. Switches could be located strategically to avoid such a false detection scenario. In one example, three switches are placed equidistant from one another on the perimeter of earpiece 20. Increasing the number of switches to four or more would further reduce the possibility of false detection.

Note that the sensitivity of turning OFF an application (or pausing an application) is something that can be adjusted. For example, if an end user inadvertently dropped apparatus 10 from his ear, there is some interim of time in which the application could remain ON (e.g., several seconds). This would allow the user some time to put earpiece 20 back in his ear and resume the conversation. In another example embodiment, the user is afforded the option of manually terminating all applications.

The detection circuit of apparatus 10 can use any suitable power source (e.g., batteries, solar, a combination of both, etc.). Apparatus 10 can contain a small battery module that can power noise-cancelling circuitry for many days of continuous operation. Additionally, switches of apparatus 10 can draw its power from the existing Bluetooth circuitry in certain embodiments.

Note that apparatus 10 can readily use the Bluetooth communication protocol. The Bluetooth communication protocol uses a short-range wireless signal that goes from a Bluetooth device placed in the ear to a cellular phone that is located elsewhere. In operation of an example involving a cellular telephone, when wearing a Bluetooth enabled apparatus 10, an end user can hear the phone ring. The end user would answer the phone by inserting apparatus 10 into his ear. Note also that apparatus 10 can be used as part of conventional car kits, either the "Installed" or "Portable" types. Both types of kits can be Bluetooth enabled.

Apparatus 10 may also include any suitable hardware, software, components, modules, interfaces, or objects that facilitate the operations thereof. This may be inclusive of appropriate algorithms and communication protocols that allow for exchanging and/or processing audio data. In addition, one or more of switches 22, 24, and 26 may be coupled to these items. In other embodiments, some of these audio coordination features are provided external to apparatus 10 or included in some other device to achieve this intended functionality.

Apparatus 10 can also include memory elements for storing information to be used in achieving the audio operations as outlined herein. Also, apparatus 10 may include a processor that can execute software or an algorithm to perform the activities, as discussed in this Specification. Apparatus 10 may further keep information in any suitable random access memory (RAM), read only memory (ROM), erasable programmable ROM (EPROM), electronically erasable PROM (EEPROM), application specific integrated circuit (ASIC), software, hardware, or in any other suitable component, device, element, or object where appropriate and based on particular needs.

Note that with the example provided above, as well as numerous other examples provided herein, interaction may be described in terms of two, three, or four switches. However, this has been done for purposes of clarity and example only. In certain cases, it may be easier to describe one or more of the functionalities of a given set of flows by only referencing a limited number of elements. It should be appreciated that apparatus 10 (and its teachings) are readily scalable and can accommodate a large number of components, as well as more complicated/sophisticated arrangements and configurations. Accordingly, the examples provided should not limit the scope or inhibit the broad teachings of apparatus 10, as potentially applied to a myriad of other architectures.

Figure 3:
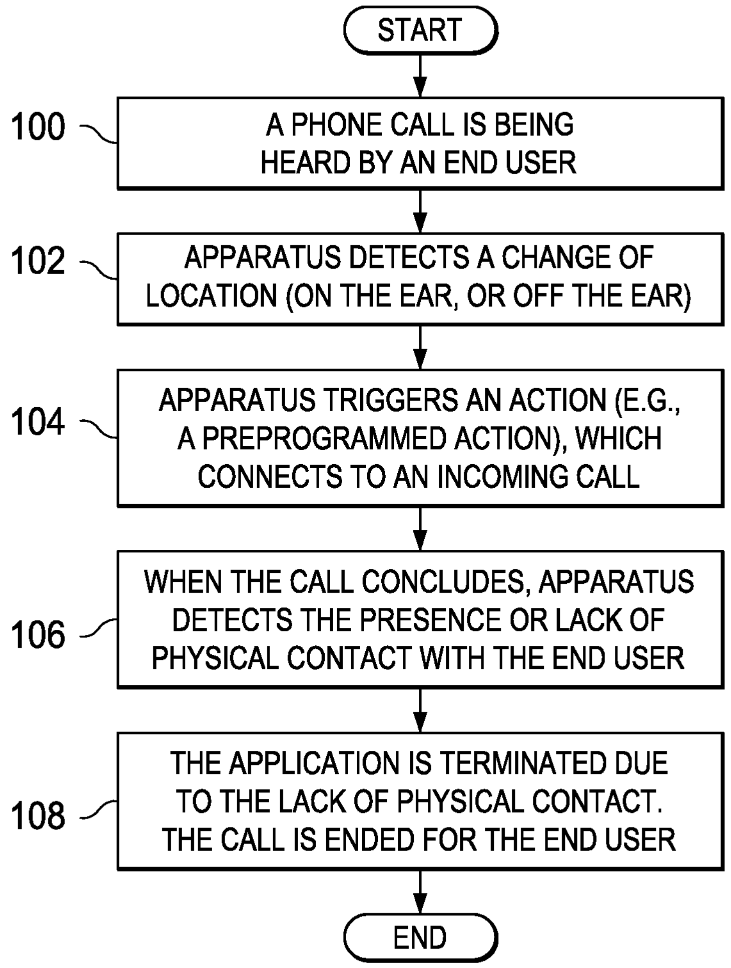
FIG. 3 is a simplified flowchart depicting an example flow for a system for audio communication.

FIG. 3 is a simplified flowchart depicting an example flow for a system for audio communication. The flow begins at step 100 where a phone call is being heard by an end user. At step 102, apparatus 10 detects a change of location of apparatus 10 (on the ear, or off the ear). At step 104, once this detection is performed, apparatus 10 triggers an action (e.g., a preprogrammed action). In this example, the action is connecting to an incoming call. When the call concludes, apparatus 10 again detects the presence or lack of physical contact with the end user at step 106. At step 108, the application is terminated due to the lack of physical contact. In this case, the call is ended for the end user.

Figure 4:
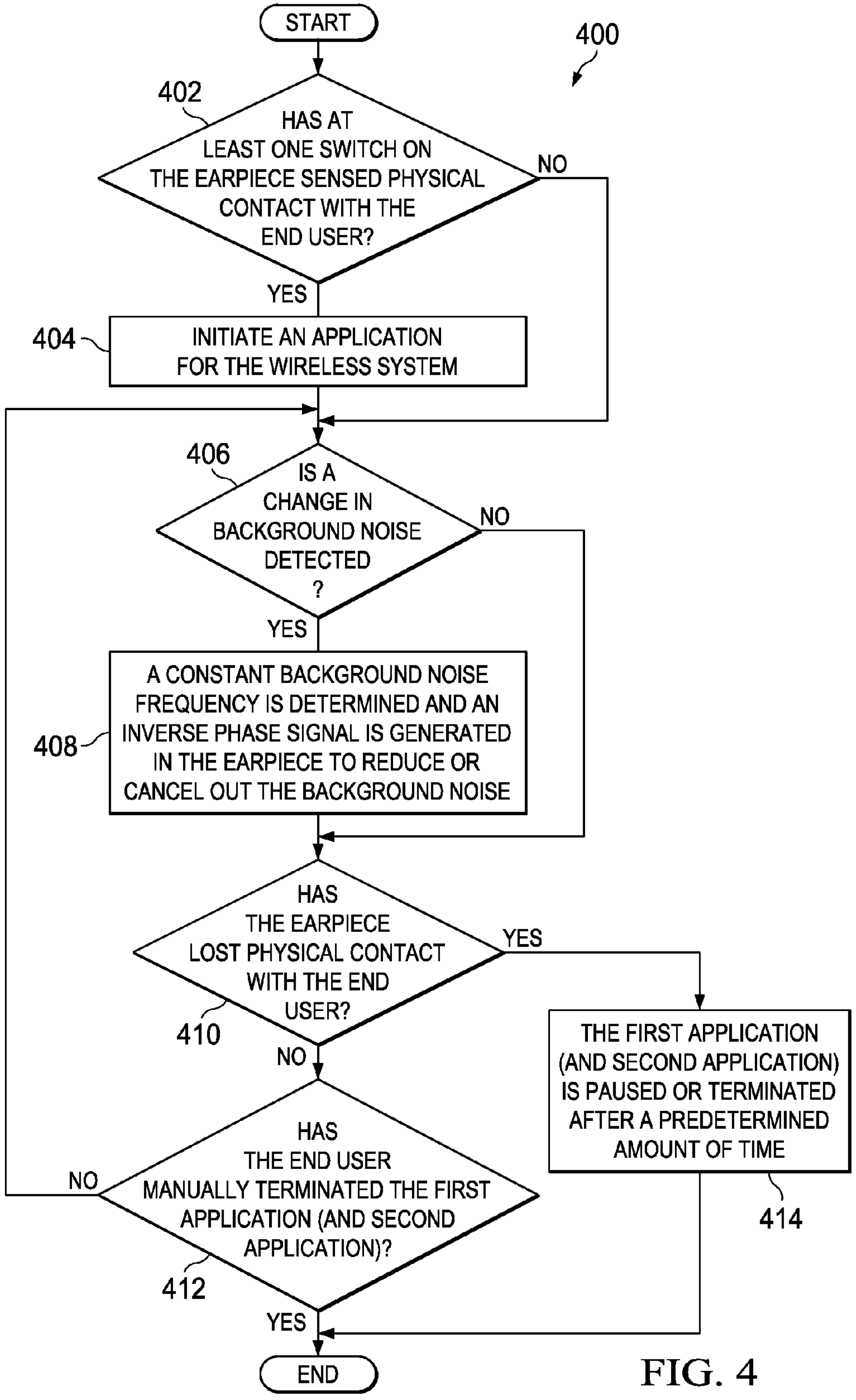
FIG. 4 is another simplified flowchart depicting an example flow for a system for audio communication.

Turning to FIG. 4, FIG. 4 is a simplified flowchart 400 illustrating example activities of audio communication. At 402, an earpiece switch senses physical contact with an end user and a first application is initiated for a wireless system. For example, switch 24, may sense physical contact with an end user. At 404, the system determines if at least one additional switch on the earpiece has sensed physical contact with the end user.

If the system determines that at least one additional switch on the earpiece has sensed physical contact with the end user, then a second application for the wireless system is initiated, as in 406. For example, switch 22 or switch 26 may sense physical contact with the end user and a second wireless application for the wireless system may be initiated. In one example, the second wireless application may be a music application, a connection to an incoming call application, a speech recognition application, or a dictation application. If the system does not determine that at least one additional switch on the earpiece has sensed physical contact with the end user, then the system determines if a change in background noise is detected, as in 408.

If a change in background noise is detected, then a constant background noise frequency is determined and an inverse phase signal is generated in the earpiece to reduce or cancel out the background noise, as in 410. If a change in background noise is not detected, then the system determines if the earpiece has lost physical contact with the end user, as in 412. If the earpiece has lost physical contact with the end user, then the first application (and second application if present) is paused or terminated after a predetermined amount of time, as in 416.

If the earpiece has not lost physical contact with the end user, then the system determines if the end user has manually terminated the first application (and second application if present). If the end user has not manually terminated the first application (and second application if present), then the system determines if at least one additional switch on the earpiece has sensed physical contact with the end user, as in 404. If the end user has manually terminated the first application (and the second application if present), then the process ends.

It is imperative to note that the steps in the preceding discussions illustrate only some of the possible scenarios that may be executed by, or within, apparatus 10. Some of these steps may be deleted or removed where appropriate, or these steps may be modified or changed considerably without departing from the scope of the present invention. In addition, a number of these operations have been described as being executed concurrently with, or in parallel to, one or more additional operations. However, the timing of these operations may be altered considerably. The preceding operational flows have been offered for purposes of example and discussion. Substantial flexibility is provided by apparatus 10 in that any suitable arrangements, chronologies, configurations, and timing mechanisms may be provided without departing from the teachings of the present invention. In a similar vein, the modular design of the illustrated FIGURES could be varied considerably. Any number of skins (for aesthetic purposes) could also be provided in conjunction with apparatus 10.

Although the present invention has been described in detail with reference to particular arrangements and configurations, these example configurations and arrangements may be changed significantly without departing from the scope of the present invention. For example, although the present invention has been described with reference to cellular communications, apparatus 10 can be used in conjunction with music applications (I-phones, I-Pods, etc.) or other auditory devices. Moreover, although communication system 10 has been illustrated with reference to particular elements and operations that facilitate the communication process, these elements and operations may be replaced by any suitable architecture or process that achieves the intended functionality of apparatus 10.

Numerous other changes, substitutions, variations, alterations, and modifications may be ascertained to one skilled in the art and it is intended that the present invention encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of the filing hereof unless the words "means for" or "step for" are specifically used in the particular claims; and (b) does not intend, by any statement in the specification, to limit this invention in any way that is not otherwise reflected in the appended claims.

What is claimed is:

1. An apparatus, comprising:

a single wireless earpiece, wherein the single wireless earpiece includes an outer ear portion and an inner ear portion that does not protrude from an ear of an end user, wherein the inner ear portion includes at least three switches that are equidistance apart, wherein each switch senses physical contact with the end user operating a wireless system, wherein the wireless system includes the wireless earpiece, wherein at least one switch from the at least three switches triggers an application to be initiated when the at least one switch detects a change in background noise to identify that the single wireless earpiece has been placed inside the ear of the end user.

2. The apparatus of claim 1, further comprising:

one or more additional switches operable to sense physical contact from the end user and initiate the application based on at least two of the switches sensing the contact, wherein the switches are equidistance apart.

3. The apparatus of claim 1, further comprising:

a microphone coupled to a body element and operable to receive voice data from the end user.

4. The apparatus of claim 1, wherein the application is a preprogrammed action, and wherein the application is selected from the group consisting of a music application, a connection to an incoming call application, a speech recognition application, and a dictation application.

5. The apparatus of claim 1, wherein the switches trigger pausing or turning the application off in response to a lack of contact from the end user.

6. The apparatus of claim 1, wherein the switches are capacitance switches.

7. The apparatus of claim 1, wherein each switch is a touch switch, a pressure switch, a frequency switch, a temperature switch, a voltage switch, or a motion switch.

8. The apparatus of claim 1, wherein the apparatus operates in conjunction with a cellular telephone.

9. The apparatus of claim 1, wherein the apparatus operates in conjunction with a portable music device.

10. The apparatus of claim 1, wherein the apparatus operates in conjunction with a desktop phone or a domestic cordless phone.

11. The apparatus of claim 1, wherein each switch includes a frequency component that detects a change in background noise when the ear of the end user is sealed off.

12. The apparatus of claim 11, wherein the apparatus determines a constant background noise frequency and sends an inverse phase signal to cancel out the background noise.

13. The apparatus of claim 1, wherein the apparatus further includes software that dictates that the application remains on even if there is no contact from the end user for a time interval.

14. The apparatus of claim 1, wherein the apparatus further includes software that allows the end user to manually terminate the application.

15. A method, comprising:

triggering an application to be initiated for a wireless device when physical contact with an end user is detected at a single earpiece, wherein the single earpiece includes an outer ear portion and an inner ear portion that does not protrude from an ear of the end user, wherein the inner ear portion includes at least three switches that are equidistance apart and each switch senses the physical contact with the end user; and triggering a second application to be initiated when at least one switch from the at least three switches detects a change in background noise to identify that the wireless earpiece has been placed inside an ear of the end user.

16. The method of claim 15, further comprising:

receiving voice data from the end user via a microphone.

17. The method of claim 15, wherein the application is a preprogrammed action, and wherein the application is selected from the group consisting of a music application, a connection to an incoming call, a speech recognition application, and a dictation application.

18. The method of claim 15, wherein a lack of the contact triggers pausing or turning the application off.

19. A system, comprising:

means for detecting physical contact with an end user operating a single earpiece for an audio communication, wherein the single earpiece includes an outer ear portion and an inner ear portion that does not protrude from an ear of the end user, wherein the inner ear portion includes at least three switches that are equidistance apart and each switch senses the physical contact with the end user; and means for triggering an application to be initiated for a wireless system based on the physical contact; and means for triggering a second application to be initiated when at least one switch from the at least three switches detects a change in background noise to identify that the wireless earpiece has been placed inside the ear of the end user.

20. The system of claim 19, further comprising:

means for receiving voice data from the end user.

21. The system of claim 19, wherein the application is a preprogrammed action, and wherein the application is selected from the group consisting of a music application, a connection to an incoming call, a speech recognition application, and a dictation application.

22. The system of claim 19, wherein a lack of the contact triggers pausing or turning the application off.

* * * * *